United States Patent [19]

Friedman

[11] 4,078,562
[45] Mar. 14, 1978

[54] INFUSION PUMP WITH FEEDBACK CONTROL

[75] Inventor: Irving Friedman, New Haven, Conn.

[73] Assignee: Diana W. Friedman, New Haven, Conn.

[21] Appl. No.: 714,348

[22] Filed: Aug. 16, 1976

[51] Int. Cl.² .............................................. A61M 5/00
[52] U.S. Cl. .................................... 128/213; 128/2 S; 128/214 F
[58] Field of Search ............. 128/2 S, 2.05 R, 2.05 T, 128/2.06 F, 213, 214 E, 214 F, 230, 273, 361

[56] References Cited

U.S. PATENT DOCUMENTS

| 2,690,178 | 9/1954 | Bickford | 128/213 |
| 3,584,623 | 6/1971 | Carlisle | 128/218 A X |
| 3,599,628 | 8/1971 | Abbenante et al. | 128/2 R X |
| 3,651,806 | 3/1972 | Hirshberg | 128/214 E |
| 3,731,679 | 5/1973 | Wilhelmson et al. | 128/214 E |
| 3,871,361 | 3/1975 | Kamen | 128/2.05 R |
| 3,901,231 | 8/1975 | Olson | 128/214 F |

Primary Examiner—Dalton L. Truluck
Attorney, Agent, or Firm—DeLio and Montgomery

[57] ABSTRACT

An episodic infusion pump apparatus with feedback control for periodically administering a pharmaceutical, such as oxytocin or the like, to induce labor in a pregnant woman. The drug is administered at periodic intervals except during labor contractions or when the fetal heartrate indicates fetal distress.

15 Claims, 5 Drawing Figures

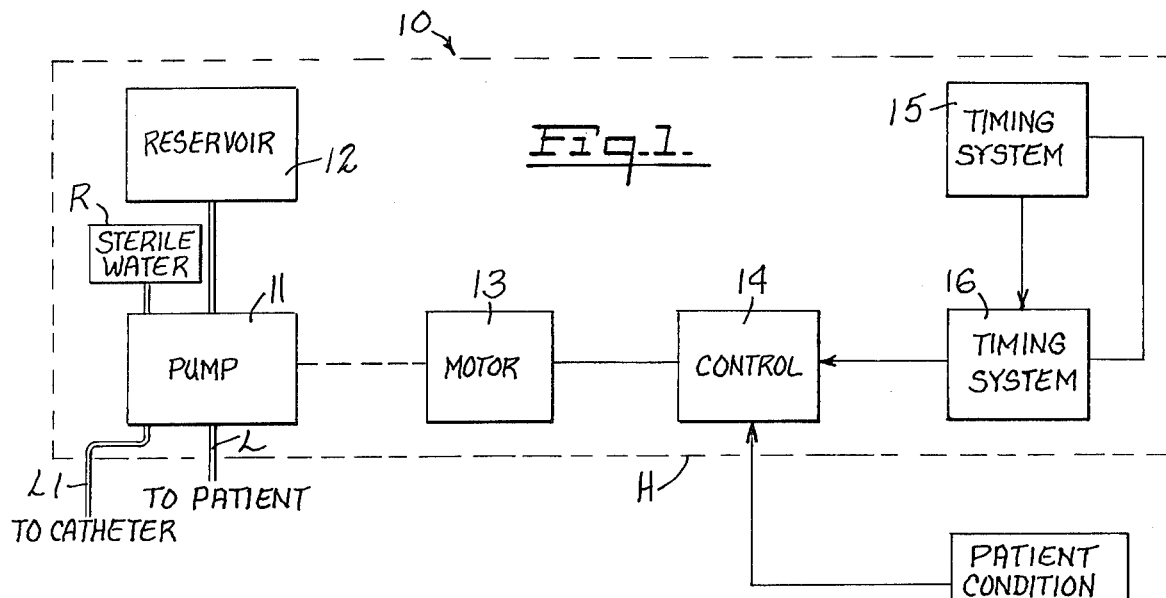
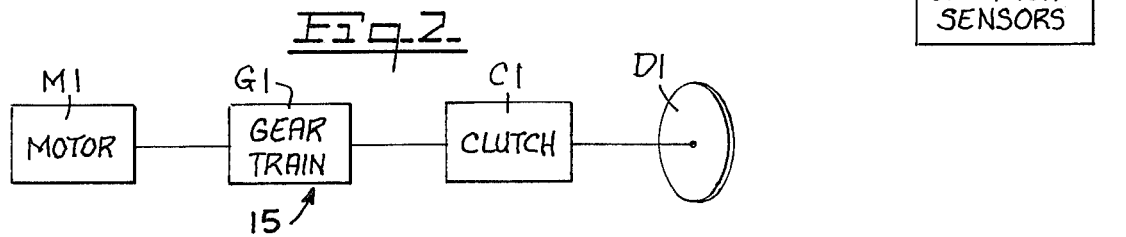
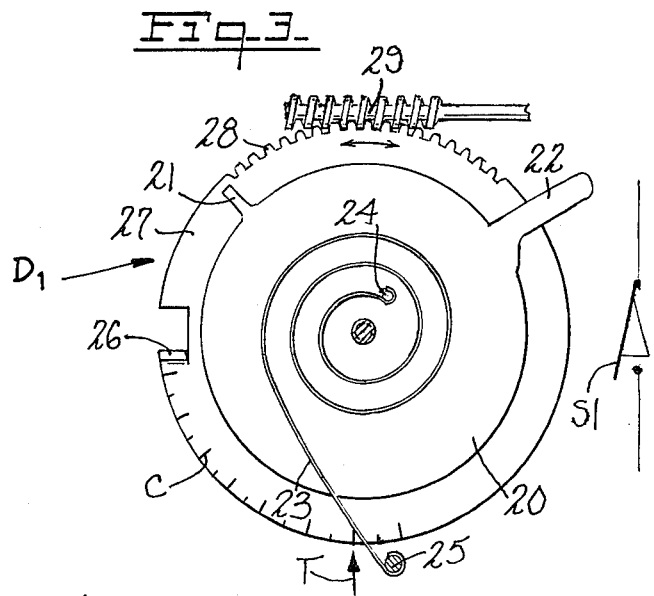
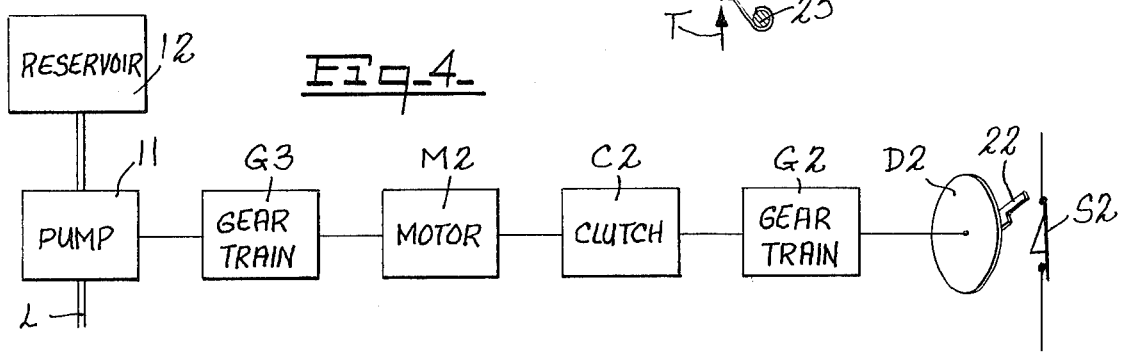

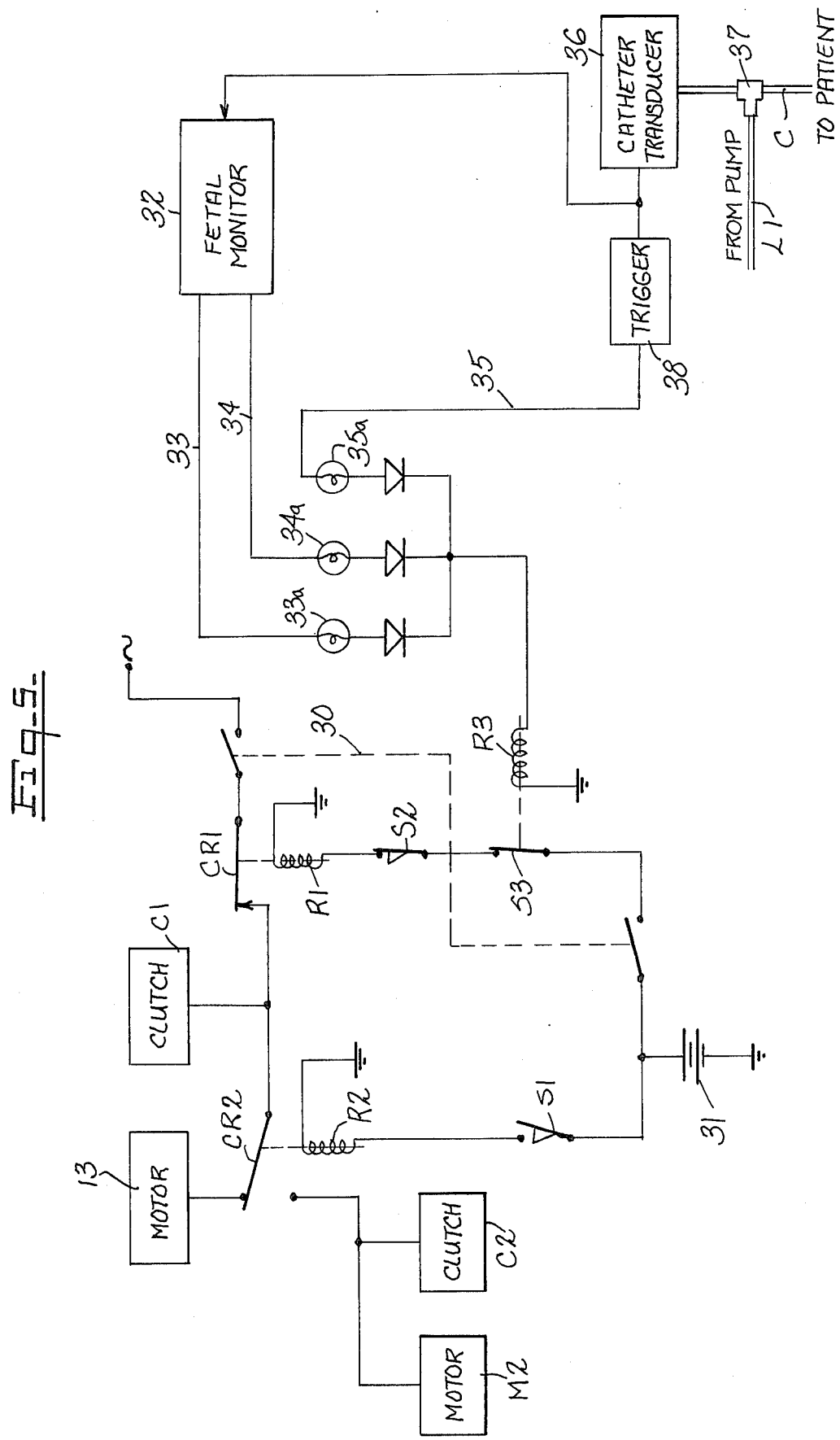

INFUSION PUMP WITH FEEDBACK CONTROL

This invention relates generally to the field of infusion pumps and to such pumps having feedback control effective for stopping infusion during predetermined conditions.

The induction of labor by continuous infusion of oxytocin as now practiced has two major deficiencies. The drugs are continuously administered which is foreign to the manner in which the body itself releases natural labor-inducing hormones into the blood stream. Also, known infusion devices have no satisfactory capability for control in response to conditions of the patient or fetus.

The uterine muscle is relatively refractory, that is, insensitive to stimulation, for a brief period of time following a contraction. This permits a rest period between contractions and reduces the likelihood of a prolonged contraction or too frequent contractions, either of which is potentially injurious to mother and/or fetus.

During normal labor the body releases the labor-inducing hormone, oxytocin, into the blood stream at periodic intervals. The released oxytocin has a short life in the blood stream having a half life estimated at about four minutes for pitocin and even less for prostoglandin, neither of which is stored by the uterine muscle.

When oxytocin is administered by a physician to induce labor by known apparatus, by continuous infusion, the delivery of oxytocin continues even during a prolonged or excessively strong contraction or during a contraction following too closely after the preceding contraction. Either condition jeopardizes both the mother and the fetus. Known infusion apparatus continues administering oxytocin during the refractory period, when it is neither stored by the uterus nor effective in stimulating it. This is particularly undesirable with infusion of agents such as prostoglandin, the use of which is limited by dose related toxicity.

It is therefore desirable to have an apparatus capable of providing periodic infusion of oxytocin or other labor-inducing drugs for a predetermined period of time and at predetermined intervals and which is further capable of stopping administration of the drug during a contraction and for an interval thereafter when the uterine muscle is refractory.

It is therefore an object of this invention to provide a new and improved episodic infusion pump for administering labor-inducing drugs to a pregnant woman.

It is a further object to provide an infusion pump that suspends administration of labor-inducing drugs during labor contractions or during fetal distress, and for a predetermined period of time thereafter.

It is yet another object of the invention to provide an infusion pump that suspends administration of the labor-inducing drugs when a fluid line such as a catheter used in sensing labor contractions is blocked.

It is yet another object of the invention to provide a new and improved method of automatically periodically administering labor-inducing drugs to a pregnant woman.

Briefly stated, the invention in one form thereof provides an episodic infusion pump having a first timing device for measuring a first time interval during which the infusion pump is not operated, that is, the interval during which no drug is being administered to the patient, a second timing device actuated at the end of the first time interval for operating the pump and for measuring a second time interval during which the drug is being supplied to the patient. At the end of the second time interval the timing devices are reset and the first device starts the cycle again. A feedback control is provided that deactivates the pump during the period of a contraction or when fetal heartrate indicates fetal distress and resets the two timing means. Following the contraction the first timing means is then reactivated which insures a period following the contraction during which no infusion is being performed. A safety device is provided to stop infusion if, in the event an intrauterine catheter is used to sense uterine contractions, the catheter becomes blocked.

The features of the invention which are believed to be novel are particularly pointed out and distinctly claimed in the concluding portion of this specification. However, the invention, both as to its organization and operation, together with further objects and advantages thereof, may best be appreciated by reference to the following detailed description taken in conjunction with the drawings, in which:

FIG. 1 is a block diagram of an episodic infusion system embodying the invention;

FIG. 2 is a detail block diagram showing a first timing system;

FIG. 3 is an elevated front view of the timing disc used in the timing mechanism shown in FIG. 3;

FIG. 4 is a block diagram of one timing mechanism used in conjunction with the episodic infusion pump system; and FIG. 5 is a diagram, partly schematic and partly in block form of an electrical network which may be used in the episodic infusion system of FIG. 1.

A system embodying the invention which periodically infuses a labor-inducing drug is set forth in block form in FIG. 1. The system 10 typically includes a pump 11 of the peristaltic type which draws liquid from a reservoir 12 and applies it to a conventional line L and needle (not shown) by which the drug is introduced to the patient. Pump 11 is periodically driven by a motor 13 through a control 14 and timing systems 15 and 16. Control system 14 may receive distress signals from patient condition sensors. The pump may also draw sterile water from a reservoir R, and supply it to a uterine catheter each pumping cycle to flush the catheter and aid in sensing blockage of the catheter if it should occur. The pump is of the type with facility for multiple channels, all operated simultaneously. Each channel utilizes a separate sterile tube which may be disposable, or may be re-sterilized after use.

The distress signals may be any one of labor contractions or fetal heartrate, or combinations thereof. Additionally an intrauterine catheter pressure signal may be utilized to determine if the catheter is blocked. The fetal heartrate and intrauterine pressure signals may be derived from a fetal monitoring system such as disclosed in U.S. Pat. No. 3,599,628. Uterine muscle contractions may also be sensed by an external abdominally mounted sensor. Fetal heartrate may also be sensed by available abdominal wall ultrasound transducers. Pressure in the uterine catheter may be derived from a transducer such as shown in U.S. Pat. No. 3,662,743 wherein a pressure-sensing transducer is coupled to an intrauterine catheter.

As will be hereinafter described, the pump is operated to alternately infuse the patient with the drug and withhold administration of the drug in periodic cycles. The length of time during which the drug is being infused and the time during which the drug is being withheld may be adjusted as hereinafter described.

The system, including the pump 11, reservoir 12, control 14, timing systems 15 and 16 and input connections for the patient sensing apparatus may be contained in a common housing generally indicated by reference H. Timing systems 15 and 16 control the intervals during which pump 11 is operated and not operated to administer the drug from reservoir 12 to the patient. Timing system 15 establishes a first time interval during which the pump 11 is not operated. At the end of the first time interval, timing system 15 actuates timing system 16 which runs for a second time interval during which the pump is operated. At the end of the second time interval, the second timing system 16 resets both the first timing system 15 and itself and the cycle begins again.

A timing system 15 which is electro-mechanical is shown in FIG. 2 and includes a synchronous motor M1, a reduction gear train G1, an electric clutch C1, and a timing disc D1. Motor M1 drives disc D1 clockwise (as shown in FIG. 3) through gear train G1 when clutch C1 is engaged. Timing disc D1 includes a plate 20 having arms 21 and 22 thereon. Arm 22 actuates switch S1 when motor M1 rotates disc D1 through a predetermined angle. A spring 23 is affixed to disc D1 at 24 and to an anchor 25 to provide a resetting means on disc D1 to return disc D1 to a start position with arm 21 abutting a stop member 26 when clutch C1 is disengaged. Stop member 26 may project from an angularly adjustable member 27 rotatable about the same axis as plate 20. For adjustment purposes member 27 has teeth 28 about the periphery thereof, engaged by a worm 29. Worm 29 rotates member 27 to adjustably position stop 26 and predetermine the off time of pump 11. Time calibrations indicated at C may be placed on member 27 to cooperate with fixed reference mark T so that the operator may easily set a time interval.

The second timing system comprises a motor M2 which drives a second timing disc D2 through clutch C2 and gear train G2. Motor M2 also drives pump 11 through gear train G3. In this system the gear train G3 is adjacent to timing disc D2 for reasons hereafter set forth. Disc D2 is arranged to operate a switch S2.

Disc D2 may be constructed identical to disc D1 and thus need not be described in detail.

As thus far described when cluth C1 is energized together with motor M1, disc D1 is driven clockwise, as viewed in FIG. 3, and arm 22 will close normally open switch S1. When switch S1 is closed, the first timing interval is terminated. When motor M2 is operated at the end of the first timing interval it drives pump 11 to draw the drug from reservoir 12 and supply it to the patient. Also, sterile water is pumped to a pressure sensing uterine catheter during such infusion cycle. At this time motor M2 also drives disc D2 through gear train G2 when clutch C2 is engaged. Arm 22 of timing disc D2 will operate a normally closed switch S2 to terminate the second timing interval.

In operation, motor M2 and clutch C2 are energized only after the first time interval predetermined by the system of FIG. 2. During the second timing interval, clutch C1 is maintained energized so that disc D1 will not be reset until the end of the infusion period. At the end of the second time interval marked by the opening of switch S2 timing discs D1 and D2 are reset as heretofore explained.

Reference is now made to FIG. 5. When an off-on switch 30 is closed, power is initially supplied to clutch C1 and motor M1 through the normally closed contact CR1 of a relay R1 when a low voltage power supply indicated at 31 energizes relay R1. At this point the first timing interval is initiated. At the end of this time interval switch S1 is closed by disc D1 to energize relay R2. Relay R2 moves its contact CR2 to a position to energize motor M2 and clutch C2 to drive disc D2 through a pre-determined time interval. At this time clutch C1 is still energized and holds switch S1 closed. When arm 22 of disc D2 opens switch S2, relay R1 is de-energized dropping out its contact CR1 and breaking the circuit between the power source and clutch C1, clutch C2 and motor M2. Disc D1 will immediately be reset by its spring 23. However, due to the positioning of gear train G2 the spring 23 of disc D2 will work against the inertia of the gear train G2, which will delay reset of disc D2 until reset of disc D1. In this manner relay R1 is maintained de-energized and its contact CR1 held open until disc D1 is reset and ready to commence a new timing interval. Timing system 15 determines the time interval between infusions, while timing system 16 determines the time length of infusion, and hence volume.

If there is no distress of the woman or the fetus, the system will continue to operate so that the pump continues to deliver the same preset volume of fluid at the preset intervals.

Another switch S3 which is operated by a relay R3 is in series with switch S2 and if opened will de-energize relay R1 and interrupt power to the entire system. Relay R3 may be operated by a signal from a fetal monitor 32 over line 33 which would be indicative of a labor contraction or a signal over line 34 which may be indicative of a fetal distress symptom such as low fetal heartrate. Also, relay R3 may be energized over a line 35 by a signal indicating that there is a blockage in the intrauterine catheter of the fetal monitor. Such signal may be derived from the transducer 36 of previously mentioned U.S. Pat. No. 3,662,743. The sterile water line L1 from the pump is connected to uterine catheter C by a T-connection 37. Each infusion cycle a small amount of water is pumped into catheter C to flush the catheter. If any blockage should occur, transducer 36 will sense the pressure increase, and supply a pressure signal to a trigger circuit, such as a Schmidt Trigger. If the pressure signal reaches a predetermined threshold, trigger 38 will fire, energizing relay R3, reset the system, and given an alarm of an adverse condition.

Indicating lamps 33a, 34a and 35a may be placed in the lines 33, 34 and 35. If the labor contractions are fairly regular lamp 33a would indicate a normal condition. However, illumination of lamps 34a and 35a would indicate a fetal distress condition or the fact that attention must be given to the catheter.

Assume now that the system is operating normally during the first timing interval and a labor contraction occurs, a signal indicative thereof is derived from the fetal monitor over line 33 and relay R3 is energized opening switch S3, relay R1 drops out opening its contact CR1, power is removed and disc D1 then resets. Thus switch S1 is not closed. The system will remain in this condition so long as switch S2 is open. Thus, so long as the contraction continues the system is inoperative. However, when the contraction has subsided relay R3 will be de-energized and switch S3 will close, thus permitting initiation of the first timing interval.

If a contraction should appear during the second interval when the pump is driven to infuse, when contact CR1 opens both timing systems, discs D1 and D2 will reset and the first timing interval will not commence until the contraction terminates.

The first timing means will generally have an adjustable time period of about 1½ to 5 minutes to define the time interval between infusions, while the second timing means may have a timing interval of about 5 to 60 seconds. The time period selected and the size of the pump tubes will determine the dosage during each pumping cycle.

The invention has been disclosed in a preferred electro-mechanical form for simplicity of disclosure. However, it is within the scope of the invention to provide digital electronic counters as timers in place of the clutch and timing disc assemblies.

The system has been disclosed as responsive to labor contractions, fetal heartrate and intrauterine catheter pressure. However, it will be apparent that the disabling of the infusion pump and holding of commencement of another infusion cycle may be made responsive to any condition inimical to the patient. As used herein the term "inimical to the patient" refers to any physical condition of the expectant mother and/or fetus or malfunction to monitoring equipment.

It may thus be seen that the objects of the invention set forth as well as those made apparent from the foregoing description are efficiently attained. While preferred embodiments of the invention have been set forth for purposes of disclosure, modifications to the disclosed embodiments of the invention as well as other embodiments thereof may occur to those skilled in the art. Accordingly, the appended claims are intended to cover all embodiments of the invention and modifications to the disclosed embodiments which do not depart from the spirit and scope of the invention.

What is claimed is:

1. Apparatus for administering a labor-inducing drug to a patient bearing a fetus in an infusion cycle wherein there exist a time interval between infusions and an interval when the drug is infused, comprising pumping means for supplying the drug to the patient, first timing means and second timing means, said first timing means being effective to predetermine the interval between infusions, said second timing means being effective to predetermine the time of infusion, said second timing means being responsive to said first timing means timing out to actuate said pumping means, means for resetting said first timing means and said second timing means at the end of an infusion interval and for restarting said first timing means, means for sensing a labor contraction of the patient and for disabling said pumping means in response thereto, means for resetting said first timing means and said second timing means in response to a labor contraction being sensed, and means for restarting said first timing means at the end of said labor contraction.

2. The apparatus of claim 1 wherein said second timing means is reset at the end of the infusion interval subsequent to reset of said first timing means.

3. The apparatus of claim 1 wherein said pumping means is disabled by deactivating said second timing means.

4. Apparatus as defined in claim 1 wherein said first timing means comprises a first timing disc rotatable by a first synchronous motor through a first reduction gear train and a first clutch, the first clutch being proximate the first timing disc, and a first actuable switch means.

5. Apparatus as defined in claim 4 in which said first timing disc comprises a rotatable plate, a first switch actuating arm affixed to rotate with said plate adapted to actuate said first switch means, a second arm affixed to said plate adapted to abut a stop, and resilient return means for biasing said disc toward said stop.

6. The apparatus of claim 5 wherein the angular position of said stop is adjustable to predetermine the time interval between infusions.

7. Apparatus as defined in claim 5 in which said second arm is angularly adjustable around said disc.

8. Apparatus as defined in claim 1 wherein said second timing means comprises a second timing disc rotatable by a synchronous motor through a second clutch and a second reduction gear train, said second clutch being proximate said second motor.

9. Apparatus as defined in claim 8 in which said second timing disc comprises a rotatable plate, a first arm affixed to rotate with said plate, a second arm affixed to said plate adapted to abut a stop, and resilient return means for biasing said second arm toward said stop.

10. Apparatus as defined in claim 9 wherein the angular position of said stop is adjustable to predetermine the infusion time interval.

11. Apparatus as defined in claim 1 further comprising means for sensing fetal heart rate and for disabling said pumping means in response to the fetal heart rate indicating fetal distress, means for resetting said first timing means and said second timing means in response to said fetal heart rate indicating fetal distress, and means for restarting said first timing means at the end of said first heart rate indicating fetal distress.

12. Apparatus as defined in claim 1 wherein said pumping means supplies the drug to the patient through a catheter, and wherein said pumping means further supplies sterile water to the patient through said catheter during at least a portion of said second time interval.

13. Apparatus as defined in claim 12 further comprising means for sensing the pressure of said drug or said sterile water in said catheter and for indicating a blockage in said catheter in response to the pressure of said drug or said sterile water exceeding a preselected level.

14. A method of inducing labor in a patient bearing a fetus by the administration of a labor-inducing drug in an infusion cycle wherein there exist a time interval between infusions and an interval when the drug is infused comprising the steps of normally measuring a first time interval, infusing the drug to the patient for a second interval of time at the end of said first time interval, sensing a labor contraction of the patient, halting said infusion in response to said labor contraction being sensed, and continuing said infusion cycles commencing with said first time interval at the end of said labor contraction.

15. A method as recited in claim 14 further comprising the steps of sensing fetal heart rate, halting infusion in response to the fetal heart rate indicating fetal distress, and resuming said infusion cycles commencing with the first time interval at the end of the fetal heart rate indicating fetal distress.

* * * * *